US012533437B2

(12) United States Patent
Chao

(10) Patent No.: US 12,533,437 B2

(45) Date of Patent: Jan. 27, 2026

(54) MODULAR AROMATHERAPY ESSENTIAL OIL DIFFUSER

(71) Applicant: Majestic-M&A International Co., Ltd., Taipei (TW)

(72) Inventor: Hsuan-Yu Chao, Taipei (TW)

( * ) Notice: Subject to any disclaimer, the term of this patent is extended or adjusted under 35 U.S.C. 154(b) by 447 days.

(21) Appl. No.: 18/315,016

(22) Filed: May 10, 2023

(65) Prior Publication Data

US 2024/0139366 A1 May 2, 2024

(30) Foreign Application Priority Data

Nov. 2, 2022 (TW) ................................. 111211999

(51) Int. Cl.
*A61L 9/14* (2006.01)

(52) U.S. Cl.
CPC ............ *A61L 9/14* (2013.01); *A61L 2209/111* (2013.01); *A61L 2209/133* (2013.01); *A61L 2209/134* (2013.01)

(58) Field of Classification Search
CPC ................. A61L 9/14; A61L 2209/111; A61L 2209/133; A61L 2209/134; A61L 9/013
See application file for complete search history.

(56) References Cited

U.S. PATENT DOCUMENTS

2019/0060938 A1* 2/2019 Whiting .............. B05B 13/0421
2019/0192720 A1* 6/2019 Alexander .............. A61L 9/122
2020/0268926 A1* 8/2020 Chao .................... A61M 11/005

* cited by examiner

*Primary Examiner* — Maris R Kessel
*Assistant Examiner* — Aham Lee

(57) ABSTRACT

A modular aromatherapy essential oil diffuser mainly includes a universal spray module having a first end having a universal connector for docking with a commercially available aromatherapy container, a second end having a nozzle, the nozzle is disposed with an atomizing sheet, and a housing which is a shell with a shape appearance and disposed therein a storage space to be connected and accommodated corresponding to a periphery of the universal spray module, wherein a circuit board is disposed in the housing to be electrically connected to the universal spray module; a power socket is disposed on the housing to supply external power to the circuit board; and a power switch is disposed on the housing to control a switch action of the circuit board. Accordingly, the universal spray module can be easily integrated and directly installed in various housings, effectively speeding up development and improving efficiency in commercial production.

2 Claims, 12 Drawing Sheets

MODULAR AROMATHERAPY ESSENTIAL OIL DIFFUSER

BACKGROUND OF THE INVENTION

Field of the Invention

This creation relates to the technical field of an aromatherapy essential oil diffuser, especially a modular aromatherapy essential oil diffuser.

The Prior Arts

In recent years, the medical and beauty industries have developed rapidly, and people are paying more and more attention to beauty care and medical care. For example, at present, ultrasonic water oxygen machine, beauty care machine, water mist aromatherapy essential oil diffuser, essential oil diffuser, etc., have been widely used in beauty salons and ordinary families. It is mainly achieved by the principle of ultrasonic atomization. Through the high-frequency vibration action of the atomizing sheet, the essence liquid output from the container is atomized into tiny particles of water mist to diffuse into the surrounding environment.

Because the aromatherapy essential oil diffuser has simple structure, easy operation, good aromatherapy essential oil diffusion effect, and can also be used as a handicraft decoration, it is especially loved by the public and has become a small household appliance in modern life. The market demand is huge, and the industry has invested in development. The focus is not only on the product itself but also on the variety of appearance and appearance. Only in this way can it win the favor of the public who like to pursue new trends and seize market opportunities to increase the purchase rate of consumers.

The existing known aromatherapy and essential oil diffusers usually have different sizes and specifications in product shapes to suit consumers of different levels. However, the overall structural design is not perfect, and the interior lacks effective modular integration. In the face of various changes in the appearance and shape of different sizes, unless the internal spray part is rearranged and planned, the old structure cannot be directly used for installation. Practically, it is impossible to increase the speed of development and production, and it cannot meet the market demand for novelty and variety of product shapes. At the same time, it is troublesome in production to replace items one by one, and it is easy to cause waste of man-hours due to unfamiliar assembly, reduce work efficiency and increase defect rate, and then increase costs and lose market competitiveness.

The information disclosed in this "BACKGROUND OF THE INVENTION" section is only for enhancement understanding of the background of the invention and therefore it may contain information that does not form the prior art that is already known to a person of ordinary skill in the art. Furthermore, the information disclosed in this "BACKGROUND OF THE INVENTION" section does not mean that one or more problems to be solved by one or more embodiments of the invention was acknowledged by a person of ordinary skill in the art.

SUMMARY OF THE INVENTION

To achieve one or a portion of or all of the objects or other objects, the invention provides a modular aromatherapy essential oil diffuser comprising a universal spray module and a housing.

Wherein, the universal spray module comprises a first end and a second end corresponding to the first end, wherein the first end of the universal spray module comprises a universal connector for docking with an aromatherapy container which is commercially available, the second end comprises a nozzle, the nozzle is disposed with an atomizing sheet, and a fuel tank is connected between the universal connector and the nozzle.

The housing is a shell with a shape appearance, and a storage space is disposed within the housing to be connected and accommodated corresponding to a periphery of the universal spray module, wherein an air outlet is disposed on the housing, and a circuit board is disposed in the housing to be electrically connected to the universal spray module; a power socket is disposed on the housing to supply external power to the circuit board; and a power switch is disposed on the housing to control a switch action of the circuit board.

Wherein, the housing is a barrel, a cylindrical body, an egg-shaped body, an L-shaped body, a circle body, a round block body, a square body, a sphere, an ellipsoid, or a polygonal block.

Wherein, the universal connector is in a cylindrical shape, and the fuel tank is connected between the first end and the second end; the universal connector comprises a front connecting opening, an internal thread and a bottom groove for disposing therein a first sealing ring, wherein the front connecting opening, the internal thread and the bottom groove are sequentially disposed inwardly at the first end; and the nozzle comprises an oil control plug disposed within an opening of the second end, a placement ring disposed on the opening of the second end and placed therein a gasket and the atomizing sheet, and a nozzle cover correspondingly disposed on and connecting to the second end.

Wherein, the placement ring is formed integrally on the nozzle cover; the nozzle cover is further disposed with an enlarged outer cover, which is screwed and locked on the second end of the universal spray module; the housing comprises a reinforced diffusion mechanism disposed between the nozzle and the air outlet; the reinforced diffusion mechanism comprises a plate corresponding to the nozzle cover disposed therein an oil-absorbing cotton, and a fan disposed on a lateral of the plate and connected to the circuit board.

In an embodiment, the housing further comprises an automatic sensing component electrically connected to the circuit board.

The invention further provides a modular aromatherapy essential oil diffuser, which comprises a universal spray module and a housing, wherein the universal spray module comprises a first end and a second end corresponding to the first end, wherein the first end of the universal spray module comprises a universal connector for docking with an aromatherapy container which is commercially available, the second end comprises a nozzle, the nozzle is disposed with an atomizing sheet, and a fuel tank is connected between the universal connector and the nozzle; and the housing is a shell with a shape appearance, and a storage space is disposed within the housing to be connected and accommodated corresponding to a periphery of the universal spray module, wherein an air outlet is disposed on the housing, and a circuit board is disposed in the housing to be electrically connected to the universal spray module; a power socket is disposed on the housing to supply external power to the circuit board; and a power switch is disposed on the housing to control a switch action of the circuit board.

Wherein, the housing is a barrel, a cylindrical body, an egg-shaped body, an L-shaped body, a circle body, a round block body, a square body, a sphere, an ellipsoid, or a polygonal block.

Wherein, the universal connector is in a cylindrical shape, and the fuel tank is connected between the first end and the second end; the universal connector comprises a front connecting opening, an internal thread and a bottom groove for disposing therein a first sealing ring, wherein the front connecting opening, the internal thread and the bottom groove are sequentially disposed inwardly at the first end; and the nozzle comprises an oil control plug disposed within an opening of the second end, a placement ring disposed on the opening of the second end and placed therein a gasket and the atomizing sheet, and a nozzle cover correspondingly disposed on and connecting to the second end.

Wherein, the placement ring is integrally formed on an expansion platform which is disposed on the opening of the second end of the universal spray module, the expansion platform comprises two sides, each of the two sides is disposed with an engagement lug, and a front portion of the nozzle cover is a convex hole, an atomizing sheet press is disposed in a middle portion of the nozzle cover; and each side of a rear portion of the nozzle cover comprises an engaging hole arm, which is engaged with a corresponding one of the engagement lugs on both sides of the expansion platform; the second end of the universal spray module is in a reduced convex shape, and an inner bend part is disposed underneath the fuel tank, so that the openings of the first end and the second end of the universal spray module are at an angle to each other, wherein the opening of the first end is larger than the opening of the second end, and a connecting opening groove is further disposed on the front connecting opening for receiving therein a second sealing ring.

In an embodiment, the modular aromatherapy essential oil diffuser further comprises an automatic sensing component disposed on the housing electrically connected to the circuit board.

In an embodiment, the housing has a base, the placement port is disposed above the base, and the air outlet is disposed on a lateral of the base.

In an embodiment, the housing is wall-mounted, and the power socket is composed of a rear plug that is connected to the housing.

In an embodiment, the housing further comprises a waterproof cover that is water-tightly covered above the placement port.

Compared with existing learning structures, the advantage of the modular aromatherapy essential oil diffuser of the invention is that it can be easily installed and used directly in various housings through the universal spray module. Regardless of the shape and size of the housing, the universal spray module can be quickly placed in the correct position without the need for additional conceptualization and production, which can effectively speed up development and improve production efficiency, making the product more diverse and stylish, and meeting the practical needs of people who pursue novelty and diverse market designs.

Other objectives, features and advantages of the present invention will be further understood from the further technological features disclosed by the embodiments of the present invention wherein there are shown and described preferred embodiments of this invention, simply by way of illustration of modes best suited to carry out the invention.

BRIEF DESCRIPTION OF THE DRAWINGS

The invention will become more readily apparent to those ordinarily skilled in the art after reviewing the following detailed description and accompanying drawings, in which.

DETAILED DESCRIPTION OF PREFERRED EMBODIMENTS

Figure 1:
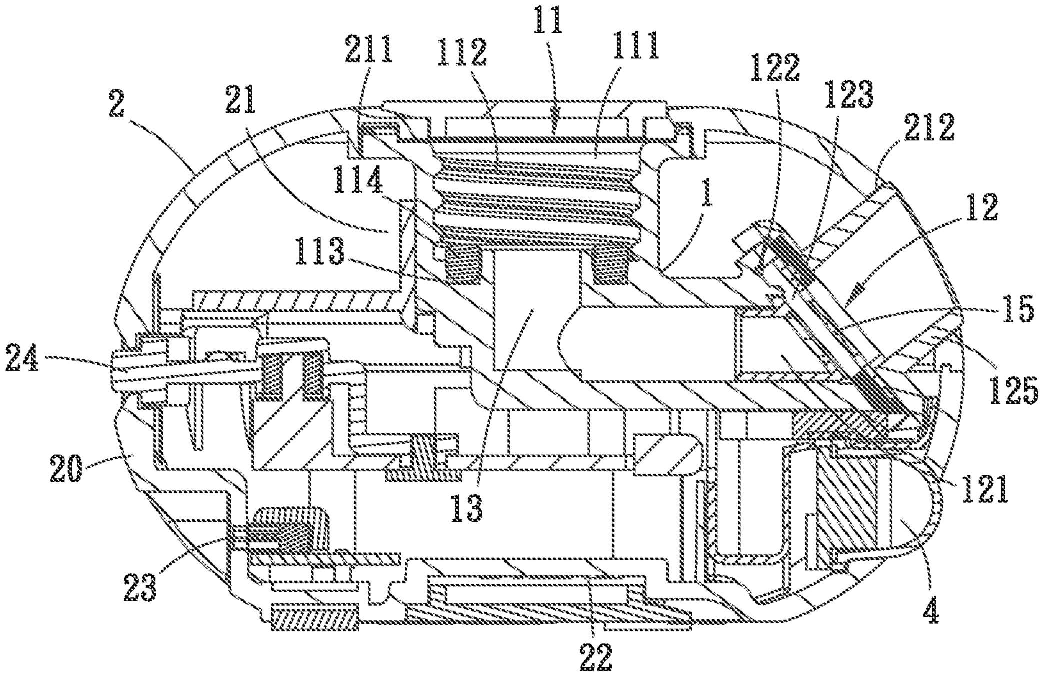
FIG. 1 is a combined sectional view of the first embodiment of the invention.
Figure 2:
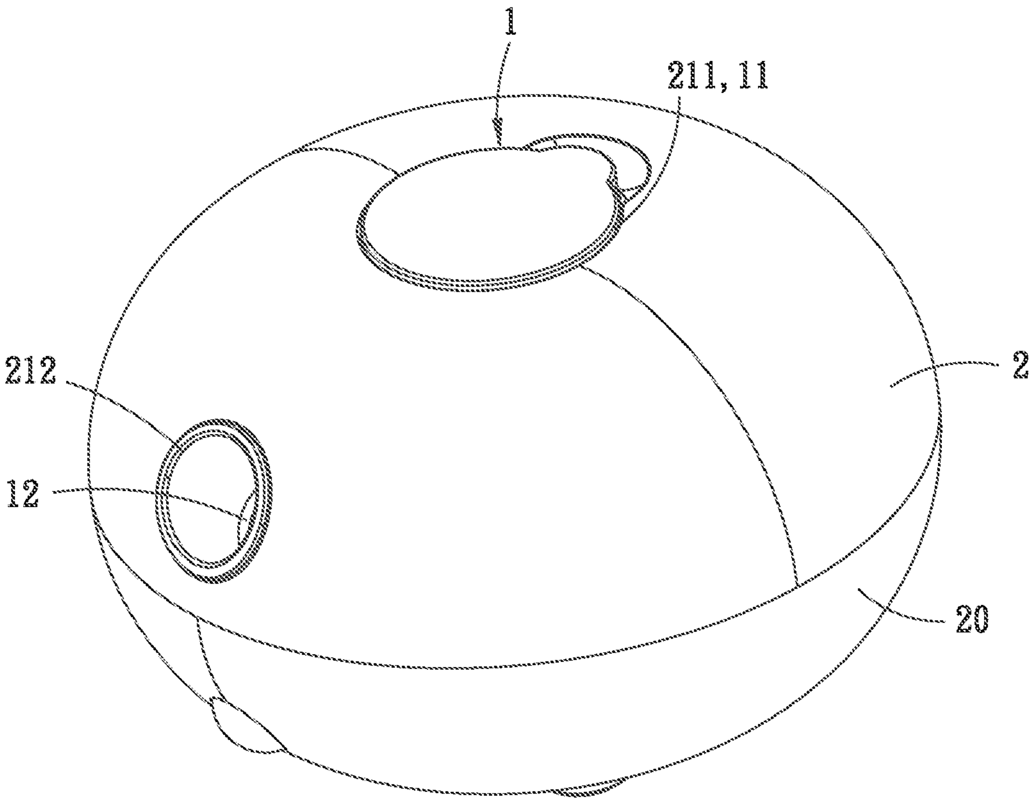
FIG. 2 is a perspective view of the appearance of the first embodiment of the invention.

To facilitate the understanding of the content of this creation and the effects that can be achieved, the specific embodiments are listed in conjunction with the diagrams, and the details are as follows: Please refer to FIGS. 1 to 9, a modular aromatherapy essential oil set up in this creation The diffuser mainly includes: a general spray module 1 and a shell 2.

One end of the universal spray module 1 has a universal connector 11 for docking with commercially available aromatherapy containers 3, and the other end has a nozzle 12 which is provided with an atomizing sheet 15. A fuel tank 13 is connected between the universal connector 11 and the nozzle 12.

The housing 2 is a shell with a shape appearance, and a storage space 21 is preset in it to be connected and accommodated corresponding to the periphery of the universal spray module 1, wherein the housing 2 is provided with a placement port 211 corresponding to the universal connector 11, an air outlet 212 is provided relative to the spray head 12, a circuit board 22 is provided in the housing 2 to be electrically connected with the universal spray module 1, and a power socket 23 is provided on the housing 2 for external power supply to the internal circuit board 22 and a power switch 24 are used to control the switching action of the circuit board 22.

Figure 3:
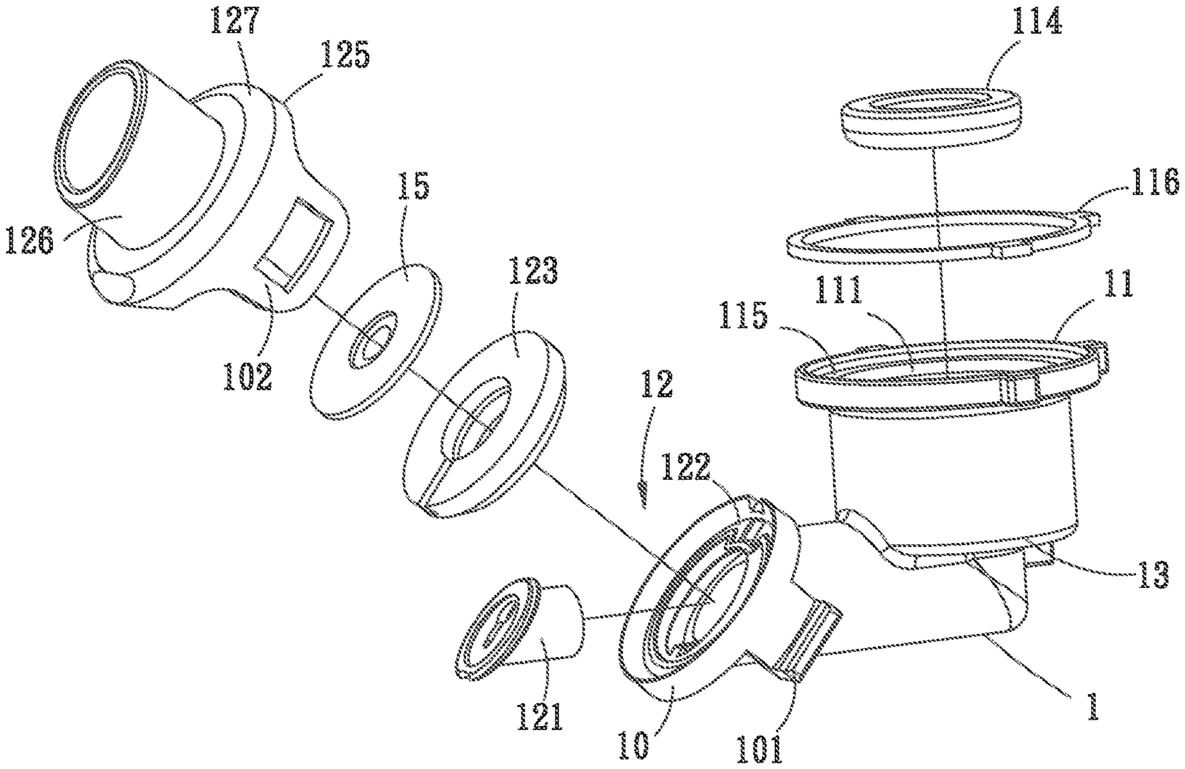
FIG. 3 is a three-dimensional exploded view of the universal spray module of the invention.
Figure 4:
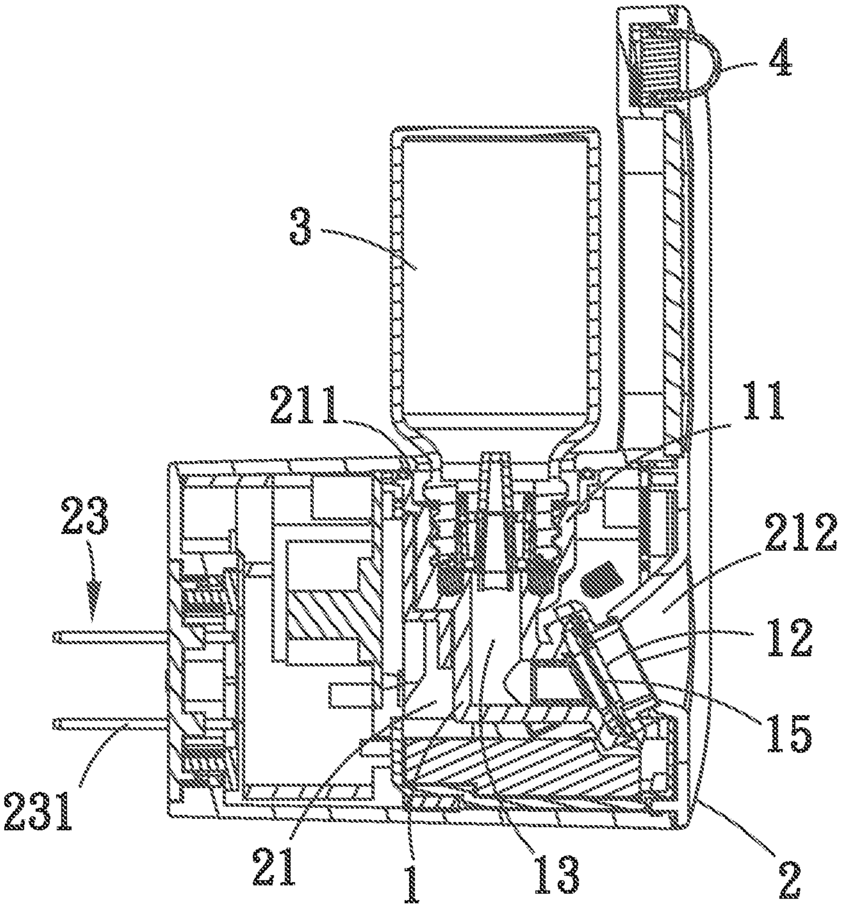
FIG. 4 is a combined sectional view of the second embodiment of the invention.
Figure 5:
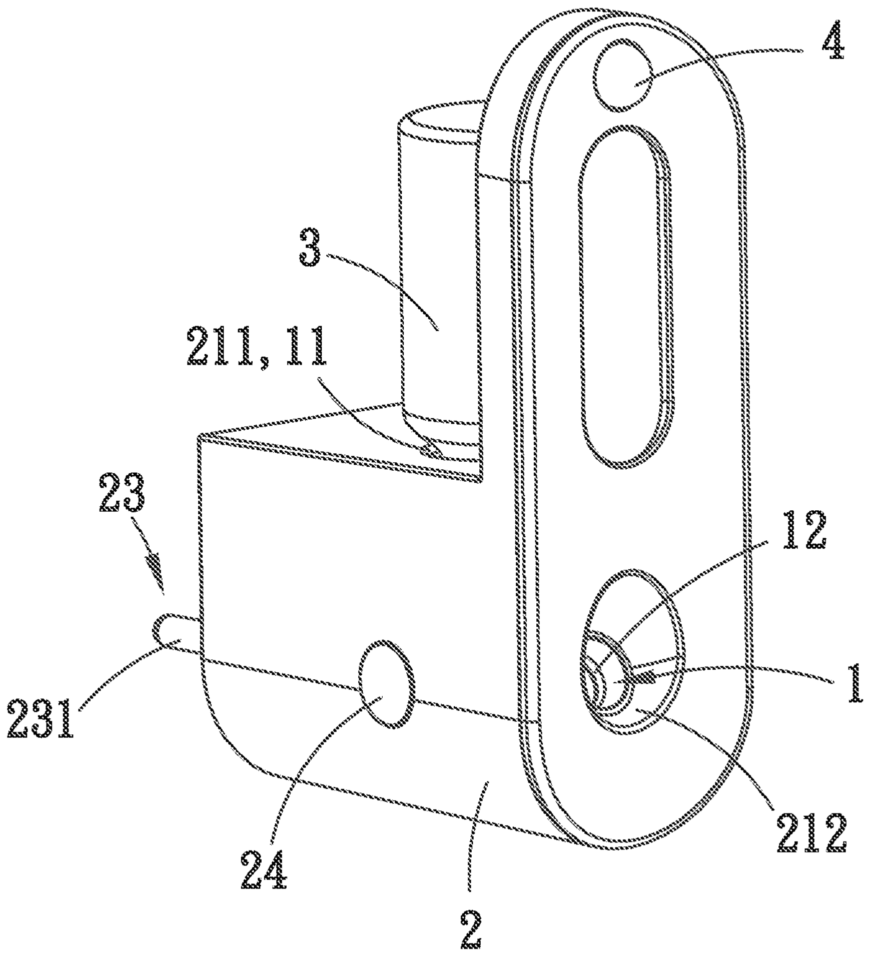
FIG. 5 is a perspective view of the appearance of the second embodiment of the invention.
Figure 6:
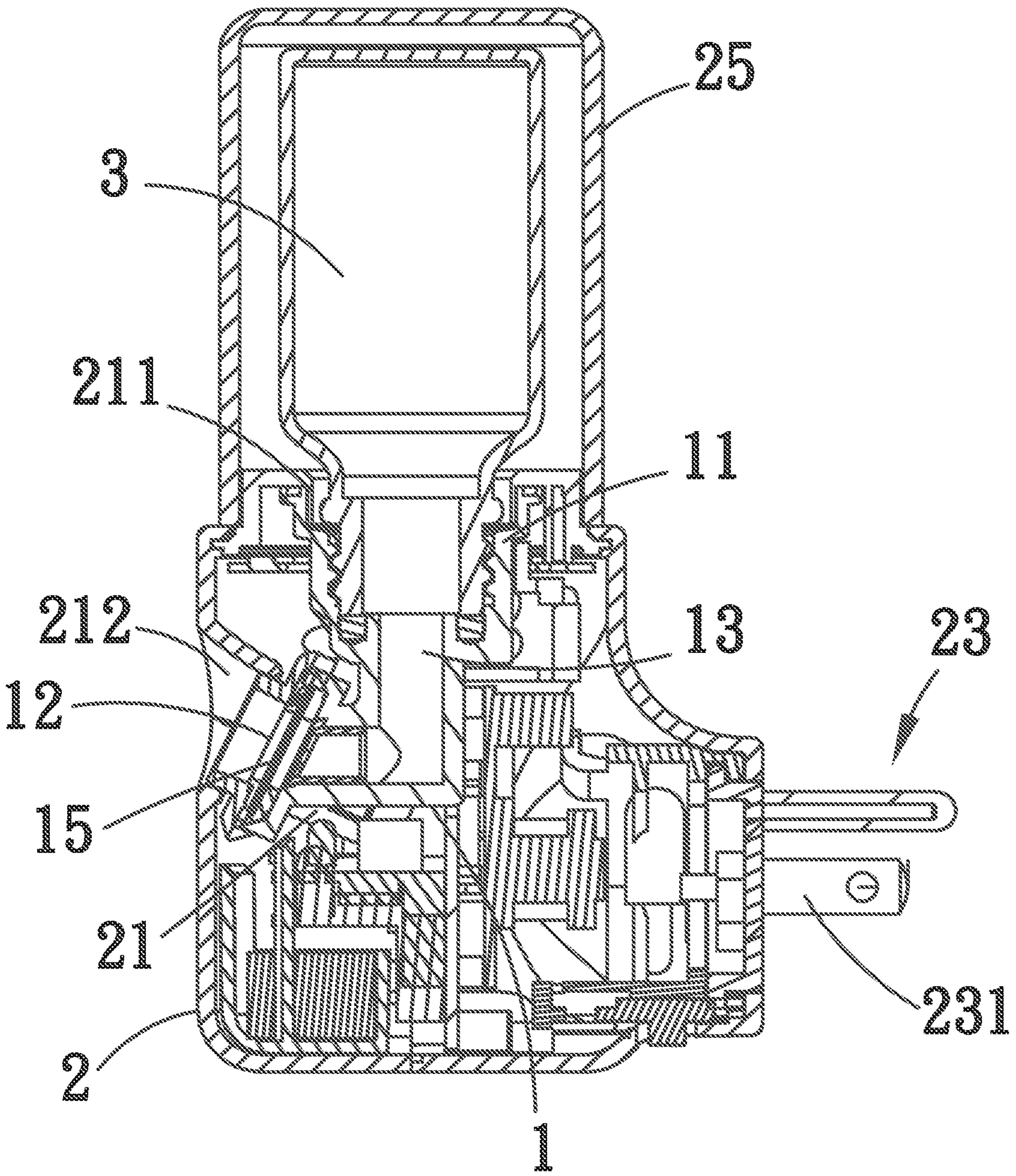
FIG. 6 is a combined sectional view of the third embodiment of the present invention.
Figure 7:
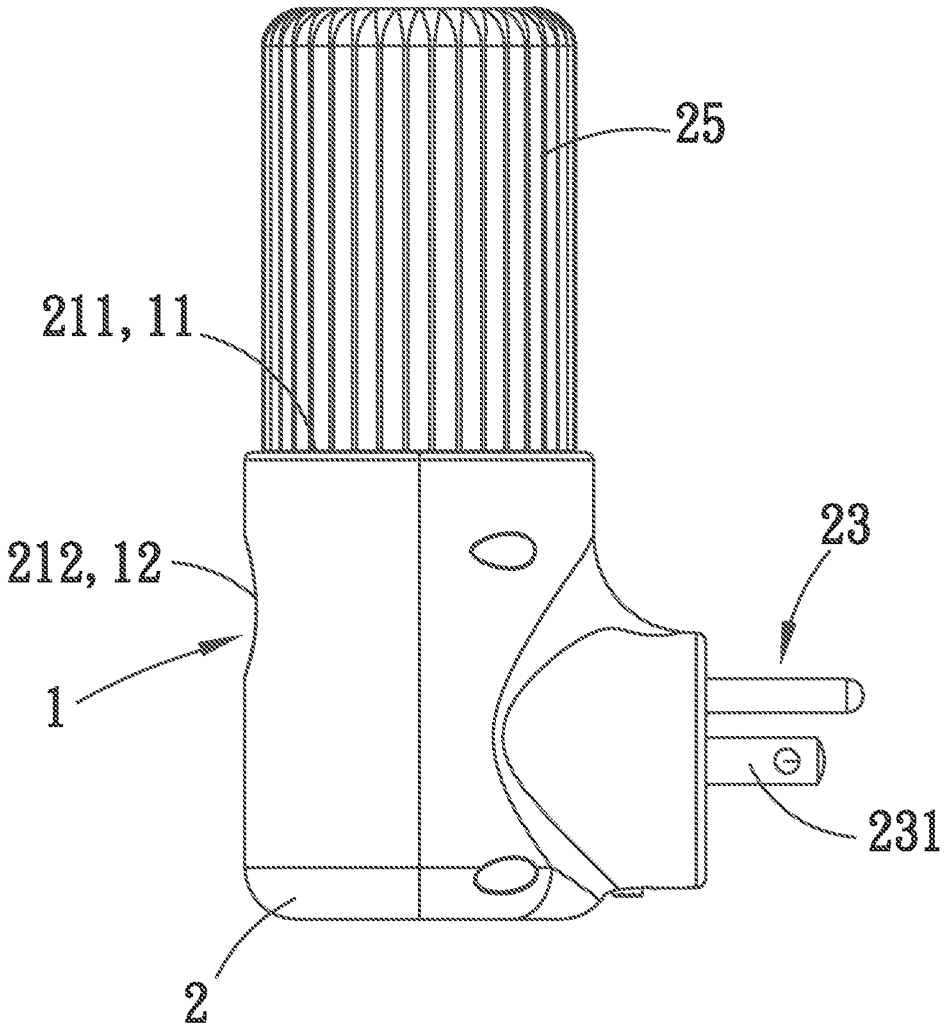
FIG. 7 is a plan view of the appearance of the third embodiment of the invention.
Figure 8:
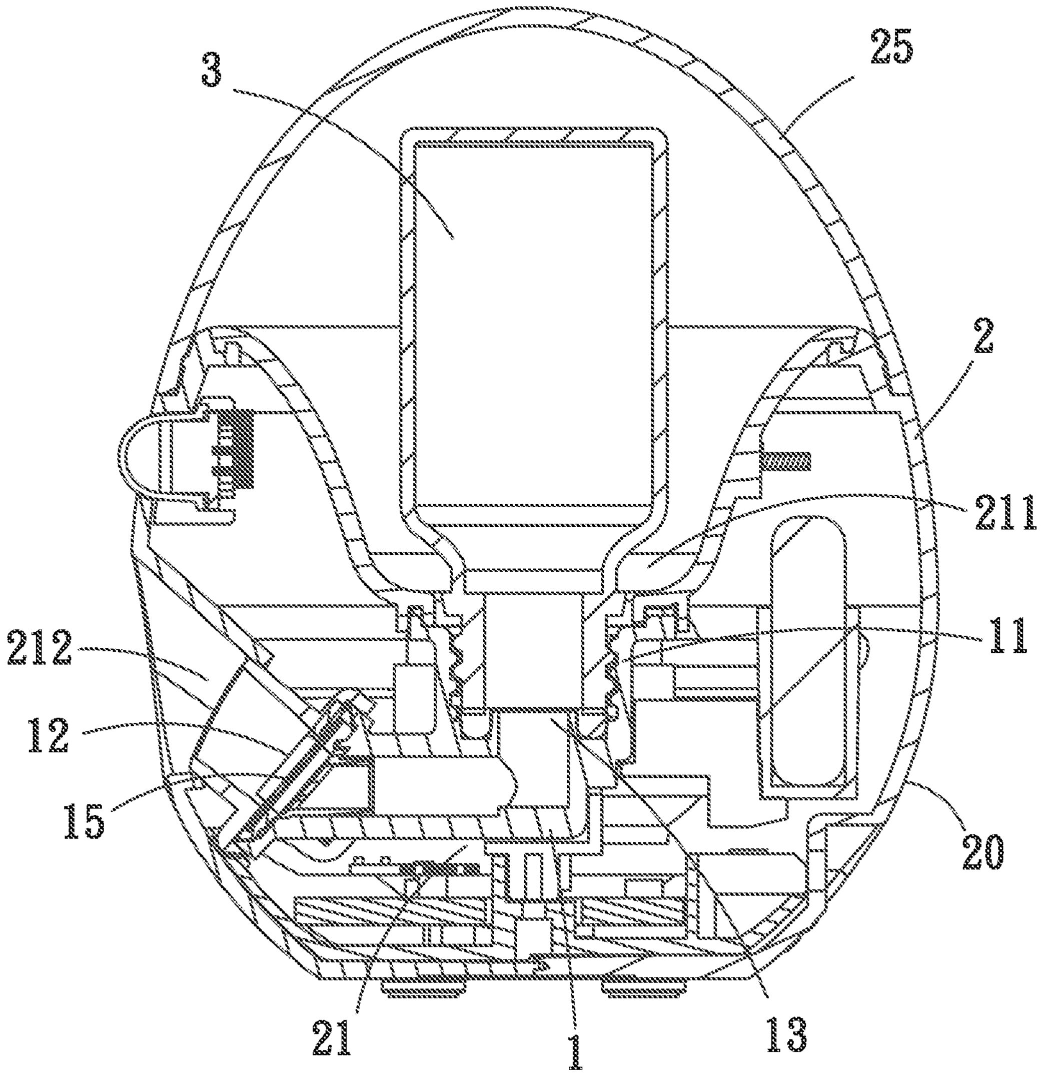
FIG. 8 is a combined sectional view of the fourth embodiment of the invention.
Figure 9:
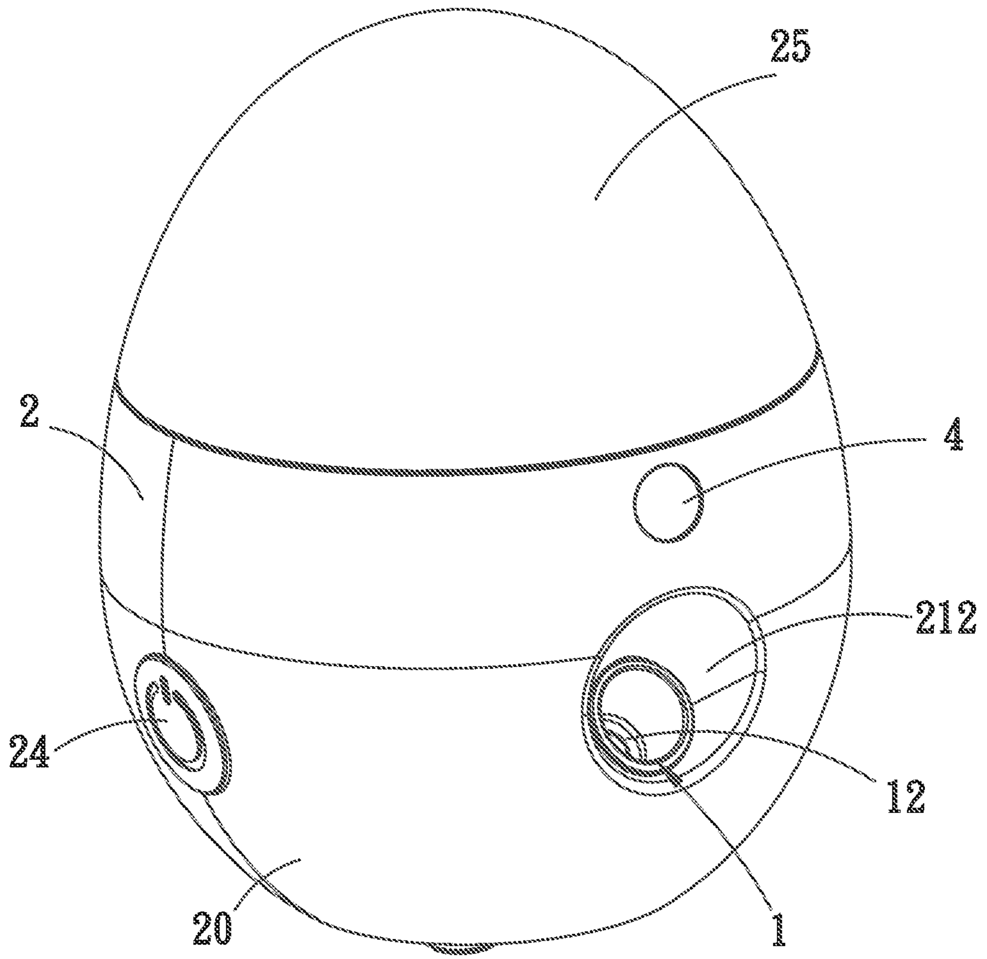
FIG. 9 is a perspective view of the appearance of the fourth embodiment of the invention.

In a preferred embodiment, as shown in FIG. 3, the universal spray module 1 includes a first end and an opposite second end thereof, the universal connector 11 is cylindrical at the first end, and the nozzle 12 is located at the second end, the fuel tank 13 is connected between the first end and the second end, and a front connecting opening 111, an internal thread 112 and a bottom groove 113 for disposing a first sealing ring 114 are provided inwardly at the opening of the first end, and thus form the universal connector 11. An oil control plug 121 is arranged in the opening of the second end, a placement ring 122 is correspondingly provided on the opening of the second end for disposing a gasket 123 and the atomizing sheet 15, and a nozzle cover 125 is assembled and connected these elements to form the nozzle 12. During implementation, the universal spray module 1 can be preset in several specifications with different heights and lengths, and the nozzle cover 125 can also be preset in various sizes for convenient installation and selection.

In a preferred embodiment, the placement ring 122 is integrally formed on an expansion platform 10 of the opening at the second end, the rear portions of two sides of the expansion platform 10 are provided with engagement lugs 101 respectively. The front portion of the nozzle cover 125 is a convex hole 126, the middle portion is an atomizing sheet press 127 connected through it, and both sides of the rear portion are respectively provided with engaging hole arms 102, so that to engage with the engagement lugs 101 on both sides of the external expansion platform 10. The second end of the universal spray module 1 is in a reduced convex shape, and an inward bend is provided under the fuel tank 13, so that the opening of the first end and the opening of the second end are arranged at an angle, and the opening of the first end is larger than the opening of the second end. A connecting opening groove 115 is provided on the front connecting opening 111 for disposing a second sealing ring 116 to increase the tightness of the assembly of the aromatherapy container 3.

In a preferred embodiment, as shown in FIGS. 1 to 12, the housing 2 is a barrel, a cylindrical body, an egg-shaped body, an L-shaped body, a circle body, a round block body, a square body, a sphere, an ellipsoid, or an irregular polygonal block, but not limited to it.

In a preferred embodiment, as shown in FIG. 1, FIG. 2 and FIG. 7, FIG. 8, the housing 2 has a base 20, the placement port 211 is located above the base 20, and the air outlet 212 is located on the base 20 on the side.

In a preferred embodiment, as shown in FIG. 4 to FIG. 7, the housing 2 is a wall-plug type, and the power socket 23 is formed by a rear plug 231 at the back of the connected body.

In a preferred embodiment, as shown in FIG. 1, FIG. 4, FIG. 8, and FIG. 9, wherein the housing 2 is further provided with an automatic sensing component 4 electrically connected to the circuit board 22, so that it can sense the human body for automatic spraying.

In a preferred embodiment, as shown in FIGS. 6 to 9, the housing 2 can be further provided with a waterproof cover 25 to cover the top of the placement port 211 with a watertight cover, so that it can be installed in the bathroom or outdoors for convenience. Waterproof won't get wet.

Figure 10:
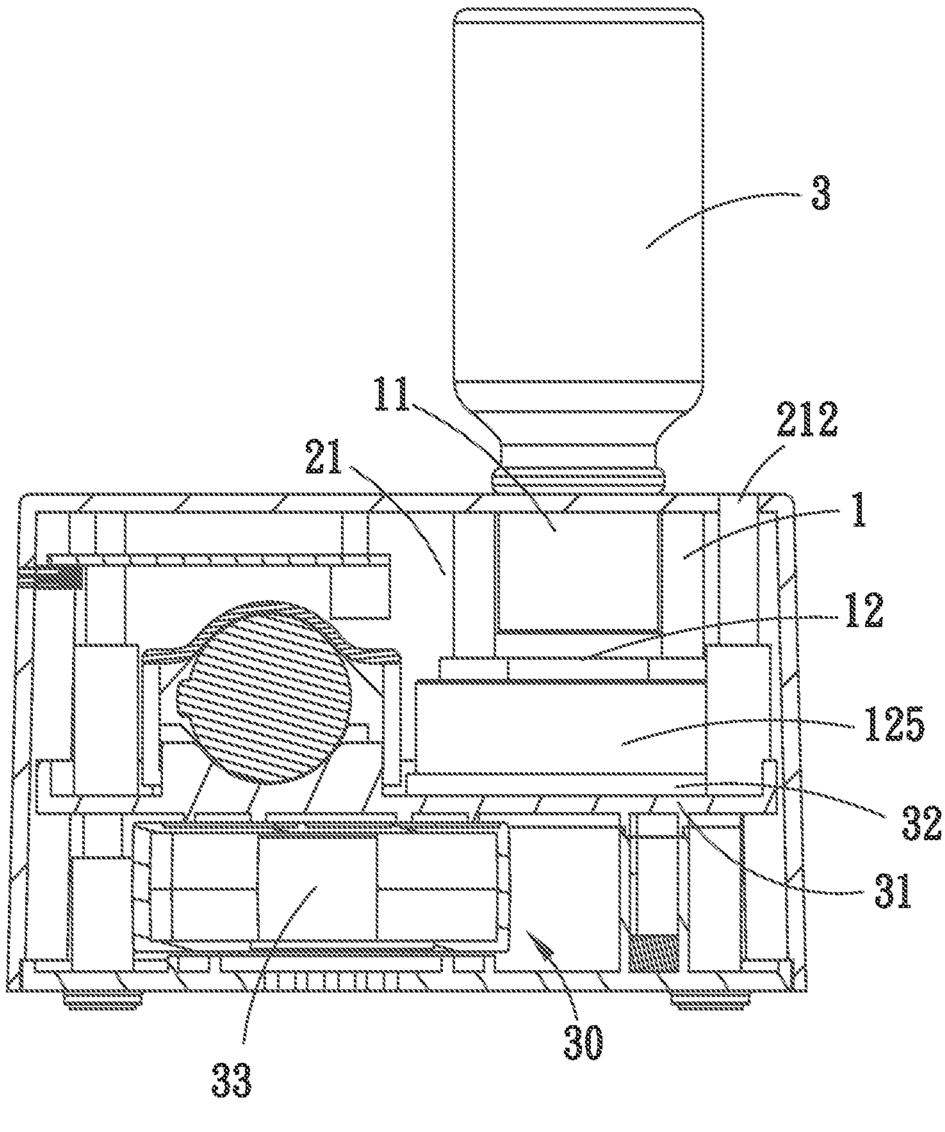
FIG. 10 is a combined sectional view of the fifth embodiment of the present invention.
Figure 11:
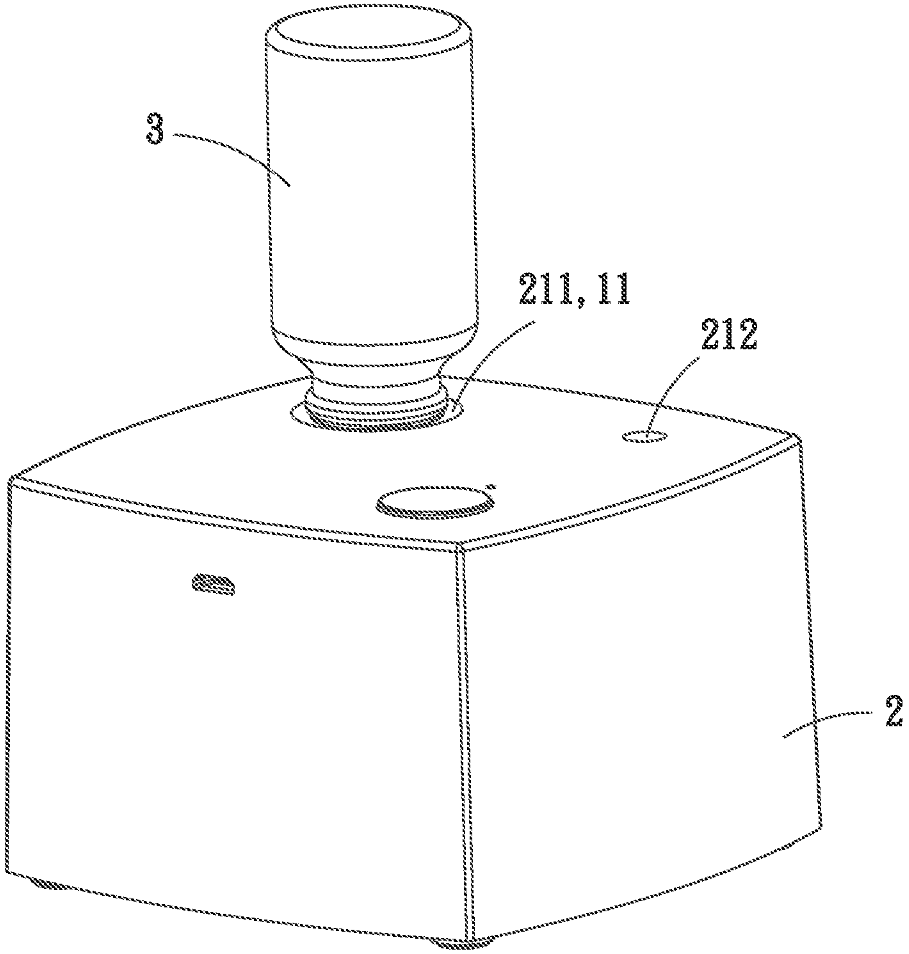
FIG. 11 is a perspective view of the appearance of the fifth embodiment of the invention.
Figure 12:
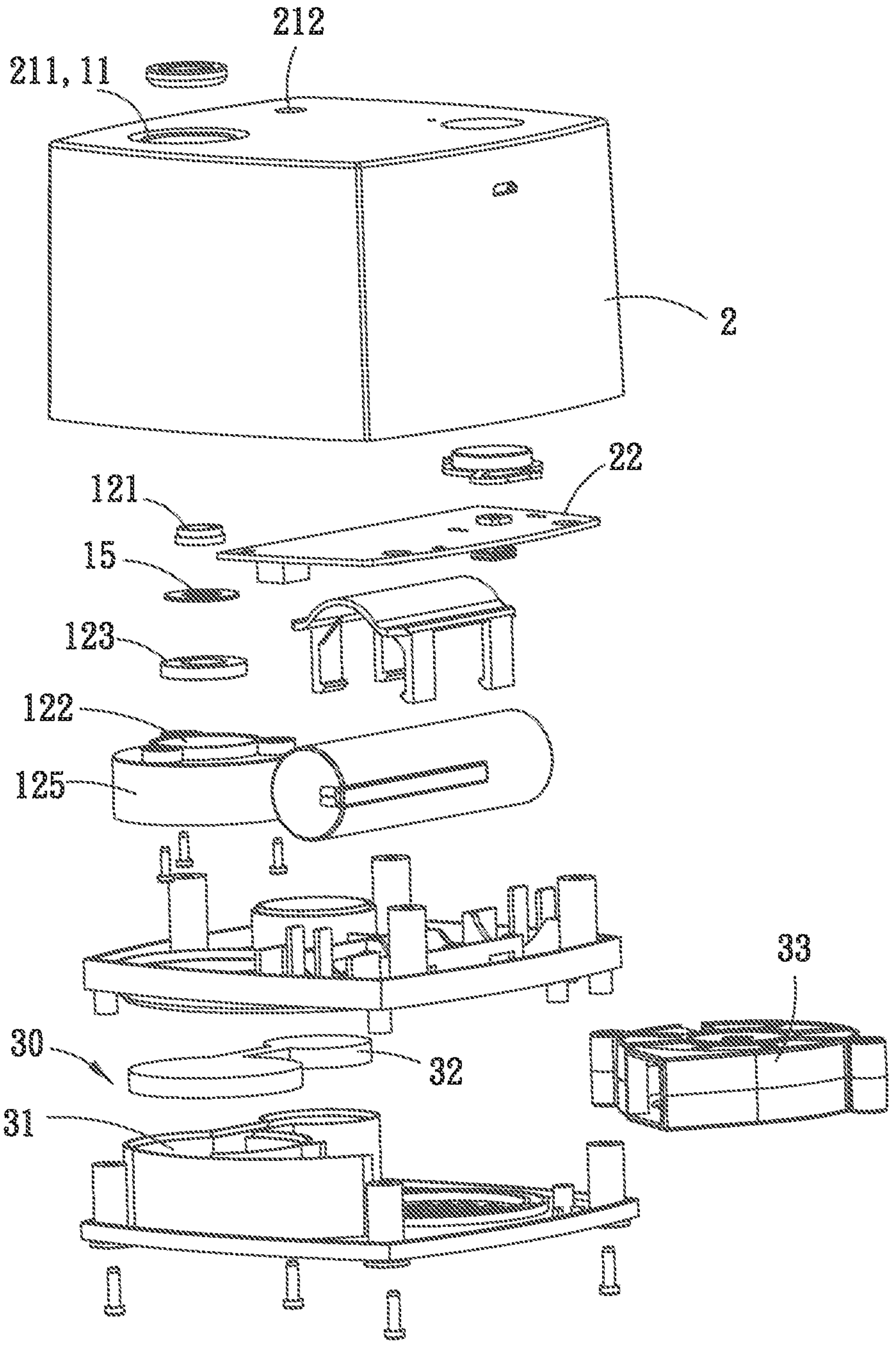
FIG. 12 is an exploded perspective view of the fifth embodiment of the invention.

In a preferred embodiment, as shown in FIGS. 10 to 12, the placement ring 122 is integrally formed on the nozzle cover 125, and the nozzle cover 125 is further set up as an enlarged outer cover that is screwed and assembled on the opening of the second end of the universal spray module 1. A reinforced diffusion mechanism 30 is provided in the housing 2 between the nozzle 12 and the air outlet 212, which includes a plate 31, an oil-absorbing cotton 32 and a fan 33. The plate 31 is correspondingly arranged under the nozzle cover 125, while the oil-absorbing cotton 32 is built in the plate 31. The fan 33 electrically connected to the circuit board 22 is provide on the side of the plate 31. During application, the essential oil can be atomized and sprayed from the nozzle 12, absorbed by the oil-absorbing cotton 32 of the plate 31, and then blown out through the air outlet 212 through the rotation of the fan 33 next to it, so as to achieve the practical purpose of enhancing the diffusion of the aroma mist.

Compared with the existing conventional structure, the advantage of the invention of a modular aromatherapy essential oil diffuser is that it can be easily installed and used in various housing 2 through the universal spray module 1, regardless of the shape and size of the housing 2. It is changeable and can be quickly selected to place the universal spray module 1 without having to bother to develop ideas and remake it. It can effectively speed up the development speed and improve the commercial production efficiency, making the types of aromatherapy and essential oil diffusers more diversified and more sculpted. It is rich to meet the practical needs of people who like to pursue trendy and various designs in multiple markets.

In summary, this invention is novel and practical and fully meets the requirements of a patent, and a new patent application is proposed. However, the above-mentioned ones are only the preferred embodiments of this creation and should not be used to limit the implementation of this creation.

What is claimed is:

1. A modular aromatherapy essential oil diffuser, comprising a universal spray module and a housing, wherein the universal spray module comprises a first end and a second end corresponding to the first end, wherein the first end of the universal spray module comprises a universal connector for docking with an aromatherapy container which is commercially available, the second end comprises a nozzle, the nozzle is disposed with an atomizing sheet, and a fuel tank is connected between the universal connector and the nozzle; and the housing is a shell with a shape appearance, and a storage space is disposed within the housing to be connected and accommodated corresponding to a periphery of the universal spray module, wherein an air outlet is disposed on the housing, and a circuit board is disposed in the housing to be electrically connected to the universal spray module; a power socket is disposed on the housing to supply external power to the circuit board; and a power switch is disposed on the housing to control a switch action of the circuit board;

wherein the housing is a barrel, a cylindrical body, an egg-shaped body, an L-shaped body, a circle body, a round block body, a square body, a sphere, an ellipsoid, or a polygonal block;

wherein the universal connector is in a cylindrical shape, and the fuel tank is connected between the first end and the second end; the universal connector comprises a front connecting opening, an internal thread and a bottom groove for disposing therein a first sealing ring, wherein the front connecting opening, the internal thread and the bottom groove are sequentially disposed inwardly at the first end; and the nozzle comprises an oil control plug disposed within an opening of the second end, a placement ring disposed on the opening of the second end and placed therein a gasket and the atomizing sheet, and a nozzle cover correspondingly disposed on and connecting to the second end; and wherein the placement ring is formed integrally on the nozzle cover; the nozzle cover is further disposed with an enlarged outer cover, which is screwed and locked on the second end of the universal spray module; the housing comprises a reinforced diffusion mechanism disposed between the nozzle and the air outlet; the reinforced diffusion mechanism comprises a plate corresponding to the nozzle cover disposed therein an oil-absorbing cotton, and a fan disposed on a lateral of the plate and connected to the circuit board.

2. The modular aromatherapy essential oil diffuser according to claim 1, wherein the housing further comprises an automatic sensing component electrically connected to the circuit board.

* * * * *